United States Patent
Hershoff et al.

(10) Patent No.: US 11,918,288 B2
(45) Date of Patent: Mar. 5, 2024

(54) APPARATUS AND METHODS FOR MEASURING FORCE REQUIRED TO REMOVE CONTACT LENS FROM AN EYE

(71) Applicant: Craig L. Hershoff, Sunny Isles Beach, FL (US)

(72) Inventors: Craig L. Hershoff, Sunny Isles Beach, FL (US); Andres Bernal, Sunny Isles Beach, FL (US)

(73) Assignee: Craig L. Hershoff, Sunny Isles Beach, FL (US)

( * ) Notice: Subject to any disclaimer, the term of this patent is extended or adjusted under 35 U.S.C. 154(b) by 648 days.

(21) Appl. No.: 17/153,984

(22) Filed: Jan. 21, 2021

(65) Prior Publication Data

US 2021/0219836 A1 Jul. 22, 2021

Related U.S. Application Data

(60) Provisional application No. 63/059,205, filed on Jul. 31, 2020, provisional application No. 62/964,285, filed on Jan. 22, 2020.

(51) Int. Cl.
*A61B 3/10* (2006.01)
*G01L 1/22* (2006.01)
*A61B 90/00* (2016.01)

(52) U.S. Cl.
CPC .............. *A61B 3/10* (2013.01); *G01L 1/22* (2013.01); *A61B 2090/064* (2016.02); *A61B 2562/0252* (2013.01); *A61B 2562/0261* (2013.01)

(58) Field of Classification Search
CPC ....... A61B 3/10; A61B 2090/064; G01L 1/22; A61F 9/0061; G02C 7/04

USPC ........................................................ 294/1.2
See application file for complete search history.

(56) References Cited

U.S. PATENT DOCUMENTS

| | | | | |
|---|---|---|---|---|
| 3,424,486 A * | 1/1969 | Clifton | ............... | B25B 11/007 294/187 |
| 3,697,109 A * | 10/1972 | Parrent | ............... | G02C 7/04 294/1.2 |
| 4,378,126 A * | 3/1983 | Procenko | ............... | A61F 9/0061 294/1.2 |
| 5,050,918 A * | 9/1991 | Kolze | ............... | A61F 9/0061 294/187 |
| 9,788,997 B2 * | 10/2017 | Hershoff | ............... | A61F 9/0061 |
| 9,913,751 B2 * | 3/2018 | Hopper | ............... | A61F 9/0061 |
| 11,376,156 B1 * | 7/2022 | Morarie | ............... | A61F 9/0061 |
| 2002/0049389 A1 * | 4/2002 | Abreu | ............... | G02C 7/04 600/318 |
| 2006/0176570 A1 * | 8/2006 | Hennegan | ............... | A61F 9/0061 359/642 |
| 2019/0231593 A1 * | 8/2019 | Keller | ............... | A61B 18/08 |

* cited by examiner

*Primary Examiner* — Paul T Chin
(74) *Attorney, Agent, or Firm* — SALIWANCHIK, LLOYD & EISENSCHENK (57) ABSTRACT

An Ocular Force Measuring Apparatus (OFMA) is provided. The OFMA can include a lens manipulator arranged on a carrier operably connected to a strain gauge load cell. The OFMA can be manipulated by hand or with an actuator mechanism. When the lens manipulator is engaged with a contact lens attached to an eye, the strain gauge load cell can measure the force required to remove the contact lens from the eye. Conversely, if a contact lens is arranged on the lens manipulator, the force required to deposit the contact lens on the eye is measureable by the strain gauge load cell.

19 Claims, 12 Drawing Sheets

APPARATUS AND METHODS FOR MEASURING FORCE REQUIRED TO REMOVE CONTACT LENS FROM AN EYE

CROSS-REFERENCE TO A RELATED APPLICATIONS

This application claims the benefit of U.S. Provisional Application Ser. No. 62/964,285, filed Jan. 22, 2020 and 63/059,205, filed Jul. 31, 2020, the disclosures of which are hereby incorporated by reference in their entirety, including all figures, tables and amino acid or nucleic acid sequences.

BACKGROUND OF INVENTION

Contact lenses for the eye are a convenient and comfortable way of improving vision. They can eliminate the need for eye glasses and are particularly advantageous when using other ocular devices, such as binoculars, diving masks, microscopes, sunglasses, protective eyewear, or other similar types of devices. Certain medical conditions can also necessitate use of contact lenses. Cataract surgery where an artificial lens cannot be implanted in the eye may require a patient to wear contacts. Contacts may also be required to treat certain types of eye diseases, such as keratoconus or damage to the cornea caused by an injury or infection of the eye.

Contact lenses are placed over the cornea of the eye and float on a layer of fluid. This layer of fluid creates surface tension and vacuum effects between the contact lens and the cornea. Removing the contact lens requires overcoming this surface tension and vacuum forces by pulling the lens away from the cornea. The amount of force necessary to remove a contact lens varies with individuals and the type of contact lens. At this time, there is no accurate device or method for measuring the amount of force necessary to remove a contact lens from the eye.

BRIEF SUMMARY

In accordance with the subject invention, the inability to measure the force required to remove a contact lens from the eye is solved by an Ocular Force Measuring Apparatus (OFMA) that can remove a contact lens from the eye and simultaneously measure the applied force necessary to remove the contact lens. With the apparatus, measurements can be obtained for individuals and with different types of hard or soft contact lenses. This can be advantageous for fitting patients with contact lenses and for research purposes. The apparatus can be a wholly or partially mechanized stand-alone device. The apparatus can alternatively be a hand-held device.

Embodiments of the subject invention can utilize a lens conveyor system that includes a lens manipulator that can contact and remove the lens from the eye. The lens manipulator can be operably connected to a carrier that supports the lens manipulator to advance the lens manipulator, mechanically or manually, towards the eye and withdraws the lens manipulator from the eye. The carrier can be further operably connected to a force measuring device, such as, for example, a strain gauge load cell or other similar device capable of accurately measuring the force used to remove a contact lens. Other features such as, for example, a lens sink for containing fluid from the eye or contact lens, one or more head rests, and a support for the carrier and/or force measuring device can also be included on the device. While particularly advantageous for measuring the force required to remove a contact lens, the apparatus can also be utilized to deposit a lens on the eye and, if required, to measure the force necessary to achieve sufficient contact for attachment.

Certain embodiments of the ocular force measurement apparatus (OFMA) and method of use provide an entirely mechanical, i.e., non-electrical, system for inserting and removing contact lenses and measuring the required force. This allows the system to be portable, easy to manipulate, and provides the user complete control over the entire process. The embodiments described herein are also amenable to being automated and certain embodiments can be motorized and/or electrically driven or electrically actuated.

In certain embodiments, the OFMA is a portable or hand-held device. With one embodiment, the OFMA can be advanced towards and away from the eye by holding the OFMA in one hand. Another embodiment includes an actuator mechanism operably connected to the OFMA. The actuator mechanism can make the OFMA more portable, since it can be securely attached to an existing support, such as a slit lamp support. The actuator mechanism can be used to advance the OFMA towards and away from the eye.

In addition, embodiments herein can be sterilized by any of a variety of methods or techniques, such as by chemical, thermal, radiation, and other techniques known in the art that are non-damaging to the materials of the embodiments of the subject invention and that do not adversely affect the lenses or user. In a particular embodiment, select components of the lens conveyor system can be removed and sterilized, such as, for example, the lens manipulator.

It should be noted that this Brief Summary is provided to generally introduce the reader to one or more select concepts described below in the Detailed Disclosure in a simplified form. This Summary is not intended to identify key and/or required features of the claimed subject matter. Other aspects and further scope of applicability of the present invention will also become apparent from the detailed descriptions given herein. It should be understood, however, that the detailed descriptions, while indicating preferred embodiments of the invention, are given by way of illustration only, since various changes and modifications within the spirit and scope of the invention will become apparent from such descriptions. The invention is defined by the claims below.

BRIEF DESCRIPTION OF DRAWINGS

In order that a more precise understanding of the above recited invention can be obtained, a more particular description of the invention briefly described above will be rendered by reference to specific embodiments thereof that are illustrated in the appended drawings. The drawings presented herein may not be drawn to scale and any reference to dimensions in the drawings or the following description is specific to the embodiments disclosed. Any variations of these dimensions that will allow the subject invention to function for its intended purpose are considered to be within the scope of the subject invention. Thus, understanding that these drawings depict only typical embodiments of the invention and are not therefore to be considered as limiting in scope, the invention will be described and explained with additional specificity and detail through the use of the accompanying drawings in which:

FIGS. 11A and 11B illustrate a hand-held embodiment of an OFMA, according to the subject invention.

DETAILED DISCLOSURE

The subject invention pertains to devices and methods for manipulating a contact lens. More specifically, the subject invention provides one or more embodiments of an ocular force measuring apparatus (OFMA) that can measure the force required to remove or deposit a contact lens on an eye.

The following description will disclose that the subject invention is particularly useful in the field of optometry, in particular, devices used to insert or remove contact lenses from the eye. However, a person with skill in the art will be able to recognize numerous other uses that would be applicable to the devices and methods of the subject invention. While the subject application describes, and many of the terms herein relate to, a use for manipulating and controlling placement of contact lenses on the eye, other modifications apparent to a person with skill in the art and having benefit of the subject disclosure are contemplated to be within the scope of the present invention.

In the description that follows, a number of terms used are utilized. In order to provide a clear and consistent understanding of the specification and claims, including the scope to be given such terms, the following definitions are provided.

The terms "contact lens" and "lens" are used interchangeably throughout the application. It should be understood that both of these terms refer to any device attached directly to the eye to correct, alter, or otherwise change the vision of the eye. In general, it refers to such devices that are rigid, such as, for example, Rigid Gas-Permeable (RGP) contact lenses. Other more specific embodiments disclosed herein are utilized with soft contact lenses. Where appropriate the application will distinguish between embodiments utilized with each type of contact lens.

The term "strain gauge load cell" is used herein to refer to a device capable of measuring a change in electrical resistance due to an applied force. Strain gauge load cells are known in the art and there are a variety of commercially available strain gauge load cells that can be employed with the embodiments of the subject invention, as described herein. Thus, embodiments of the subject invention are not limited to a particular type or configuration of strain gauge load cell. A person of skill in the art can determine an appropriate configuration of strain gauge load cell for use with the embodiments described herein.

As used herein, the term "substantially" refers to the complete or nearly complete extent or degree of an action, characteristic, property, state, structure, item, or result. For example, an object that is "substantially" in a given position including, but not limited to vertical, horizontal, or adjacent to or aligned with another object, would mean that the object is either completely in that position or nearly completely in that position. The exact allowable degree of deviation from absolute completeness may in some cases depend on the specific context. However, generally speaking the nearness of completion will be so as to have the same overall result as if absolute and total completion were obtained.

Also as used herein, the terms "longitude" or "longitudinal length" refer to the longitudinal measurement or the distance extending along the long axis. For example, the longitude or longitudinal length of a lens manipulator is the distance or direction between the proximal end to the distal end.

The terms "about" or "approximately," as used herein, are defined as at least close to a given value or either end of a range as is necessary to cover manufacturing variances, equipment tolerances, and normal variances in material, as understood by those skilled in the art.

Also, as used herein, and unless otherwise specifically stated, the terms "operable communication," "operable connection," "operably connected," "operatively attached," "cooperatively engaged" and grammatical variations thereof mean that the particular elements are connected in such a way that they cooperate to achieve their intended function or functions. The "connection" or "engagement" may be direct, or indirect, physical or remote.

It is to be understood that the figures and descriptions of embodiments of the present invention have been simplified to illustrate elements that are relevant for a clear understanding of the invention, while eliminating, for purposes of clarity, other elements that may be well known. Those of ordinary skill in the art will recognize that other elements may be desirable and/or required in order to implement the present invention. However, because such elements are well known in the art, and because they do not facilitate a better understanding of the present invention, a discussion of such elements is not provided herein.

Furthermore, reference is made throughout the application to the "proximal end" or "proximal direction" and "distal end" or "distal direction." As used herein, the proximal end or proximal direction is that end that approaches or is nearest to the eye. For example, the suction cup is at the proximal end of the lens manipulator. Likewise, the carrier is arranged in the distal end of the lens manipulator. Conversely, the distal end or distal direction of the device is that end furthest from the eye or, in the alternative, the end approaching or nearest to the actuator mechanism. For example, the distal end of the carrier can be operably connected to a strain gauge load cell.

The present invention is more particularly described in the following examples that are intended to be illustrative only because numerous modifications and variations therein will be apparent to those skilled in the art. As used in the specification and in the claims, the singular for "a," "an" and "the" include plural referents unless the context clearly dictates otherwise.

Reference will be made to the attached Figures on which the same reference numerals are used throughout to indicate the same or similar components. With reference to the attached Figures, which show certain embodiments of the subject invention, it can be seen that an Ocular Force Measuring Apparatus 100 (OFMA) of the subject invention comprises a lens manipulator 125 positioned on a carrier 150 that can convey the lens manipulator. The carrier can be operably connected to a strain gauge load cell 155. The measureable forces exerted and detected by the strain gauge load cell can be shown on a display 159. The OFMA can be a hand-held device that is manipulated to remove or deposit a lens on an eye and measures the applied force. The OFMA can also be arranged or attached on a support 200 that can be used to position the OFMA relative to an eye. A bracket 170 can secure the carrier at or about the proximal end 15 of the strain gauge load cell and be used to adjust and lock the position of the carrier and the height of the lens manipulator on the proximal end 15 of the carrier. The distal end 20 of the strain gauge load cell can be attached to an actuator mechanism 180 that can move the strain gauge load cell in two directions. Alternatively, the OFMA can be operably attached to an actuator mechanism that can be secured to a support. The strain gauge load cell 155 can be configured to measure the force required to remove a lens from the eye or, alternatively, to measure the force required to deposit a lens on the eye of a patient. Additional components, such as a lens sink 160 for containing fluid, a mechanical control 185 for the actuator mechanism, an electrical control mechanism 300 or manual control 310 for the actuator, and head rests 210 can also be included on the apparatus. Each of these general components can have one or more sub-components, which will be discussed in detail below.

The Ocular Force Measuring Apparatus (OFMA) can comprise components designed to measure the force required to remove a contact lens 15 from the or cornea of the eye. Alternatively, the components of the OFMA can measure the force required to deposit a contact lens on the surface or cornea of the eye. To obtain a measurement, the lens manipulator of the OFMA is ideally positioned so that it can approach the surface of the eye in a substantially perpendicular direction.

Figure 1:
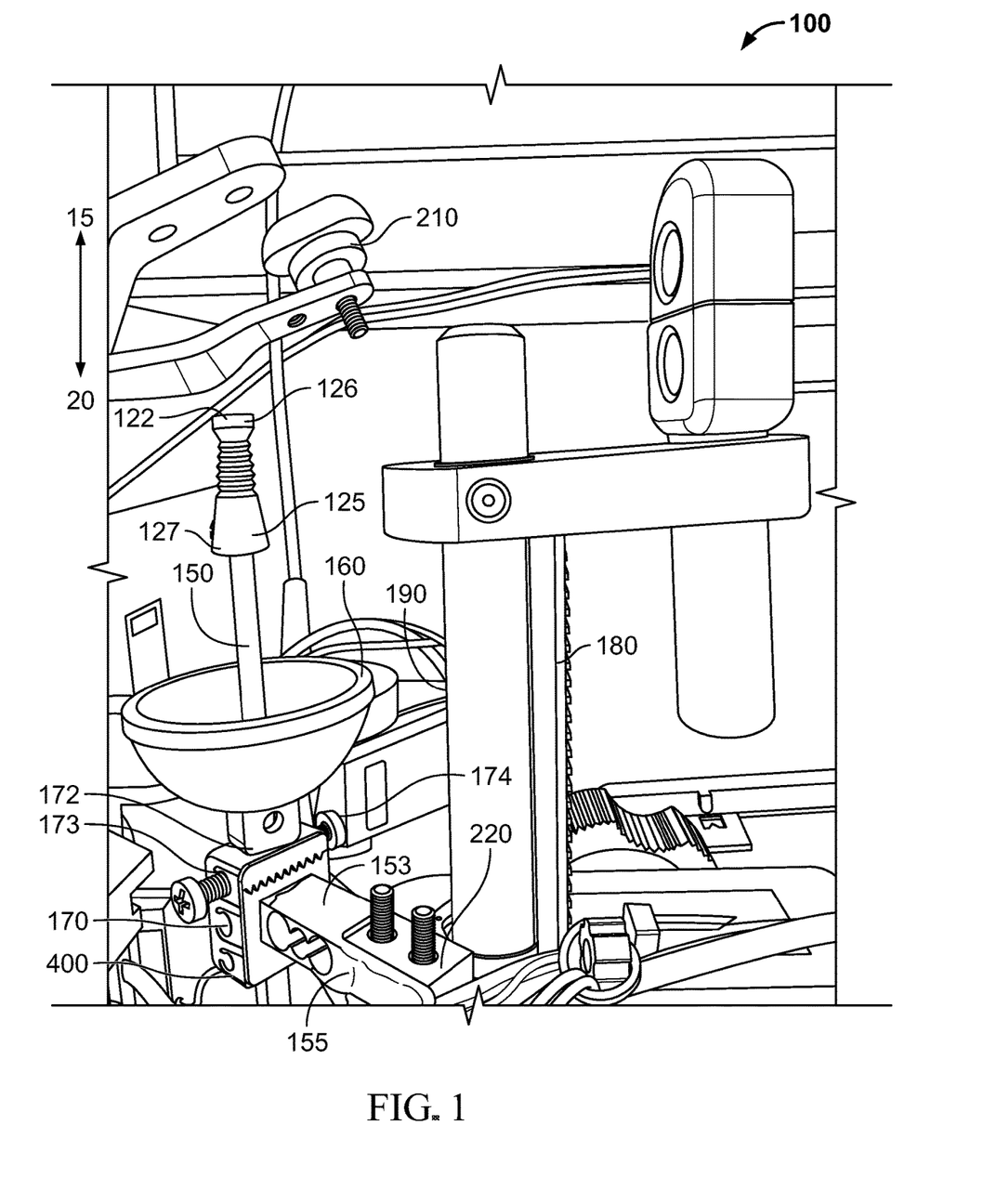
FIG. 1 shows an Ocular Force Measuring Apparatus (OFMA), according to one embodiment of the subject invention.
Figure 3:
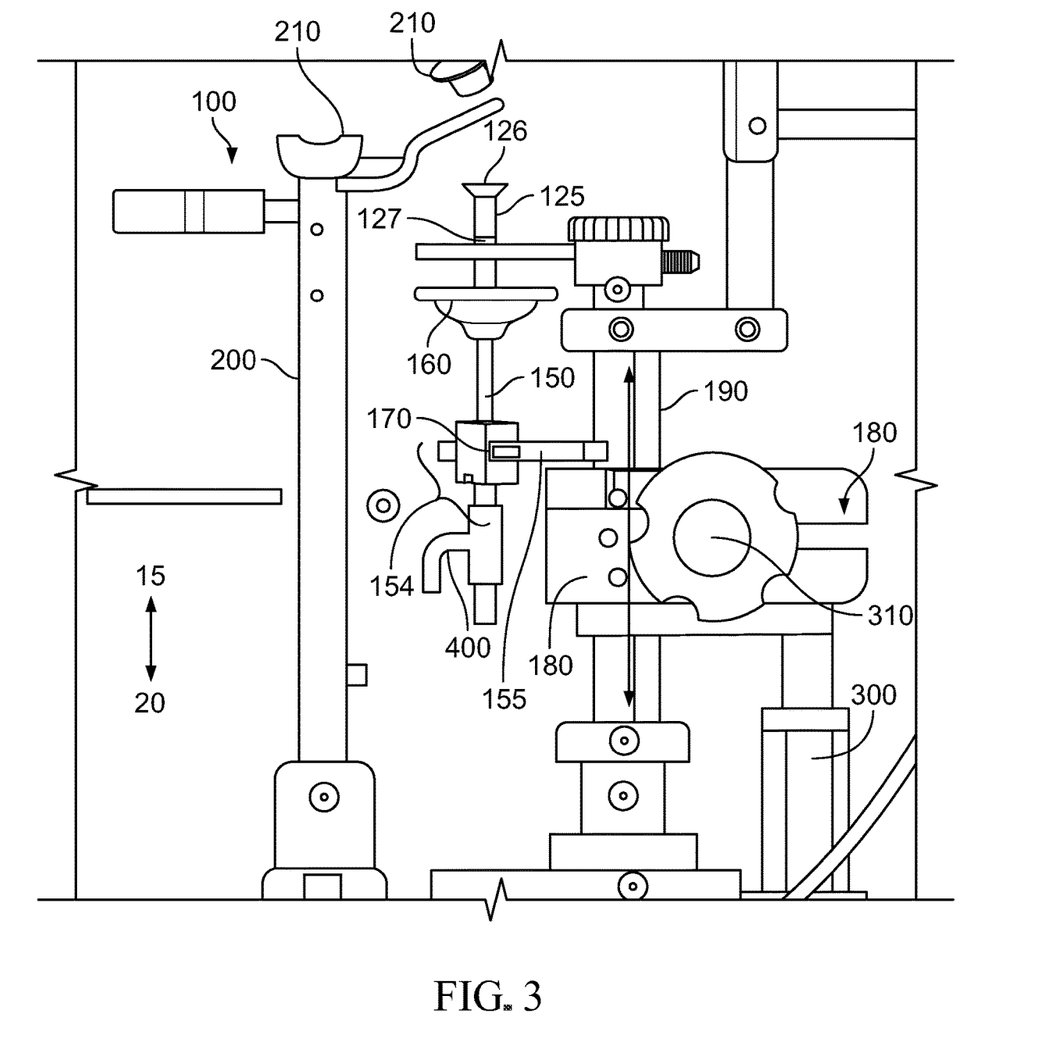
FIG. 3 shows an OFMA, according to one embodiment of the subject invention.

In one embodiment, an OFMA includes a lens manipulator 125, a carrier 150, and strain gauge load cell 155. The OFMA can be connected to a support 200 on which the head can be positioned, so that the eye is aligned with the lens manipulator. In one embodiment, the support has one or more head or face rests 210. The head and face rests can support the head and can also act as a guide to properly position the patient on the OFMA. FIGS. 1 and 3 illustrate non-limiting examples of a support with head and face rests.

Figure 2A:
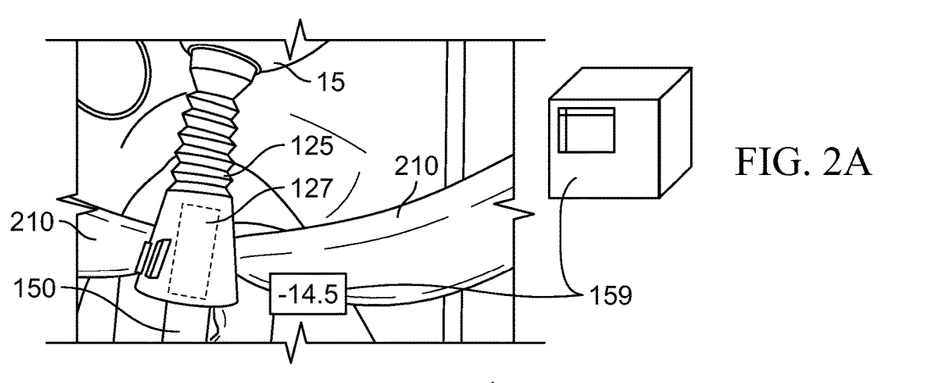
FIGS. 2A, 2B, and 2C illustrate a process by which a contact lens is removed from an eye utilizing an OFMA, according to one embodiment of the subject invention, and the force required is shown on a display.
Figure 2B:
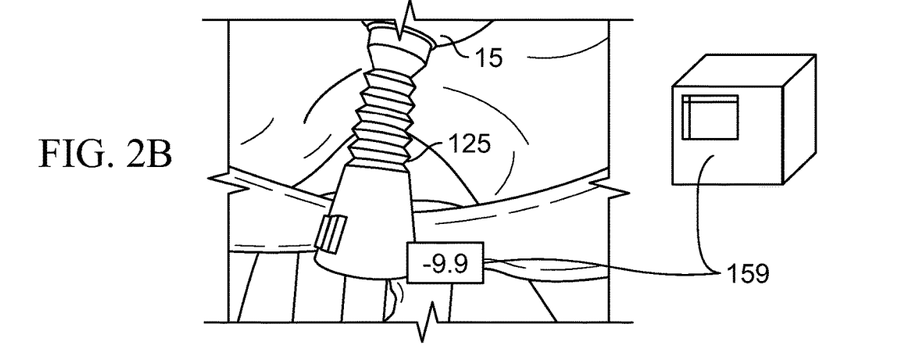

FIGS. 2A and 2B illustrate one example of the head and face rests supporting the head and aligning the eye with the lens manipulator.

Figure 12:
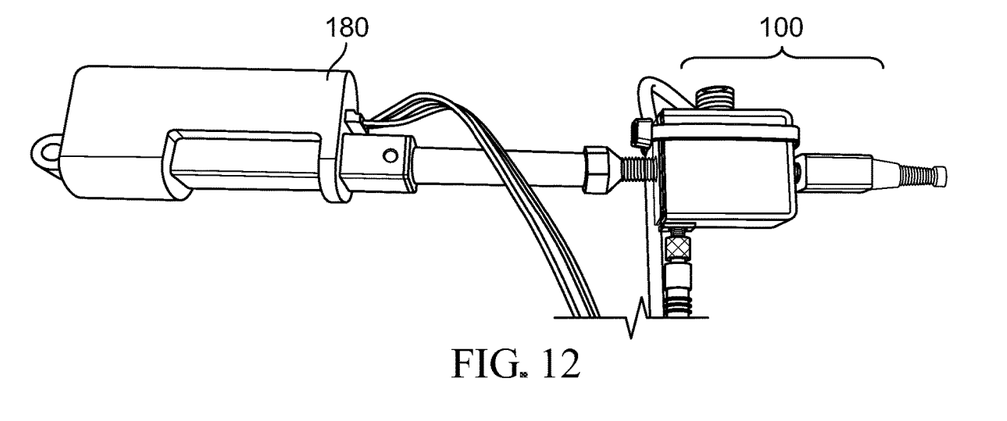
FIG. 12 illustrates an embodiment of an OFMA operably attached to an actuator mechanism. The actuator mechanism can be operably attached to a stand, support, mount or other structure that allows the actuator mechanism to move the OFMA away from or towards an eye.
Figure 13A:
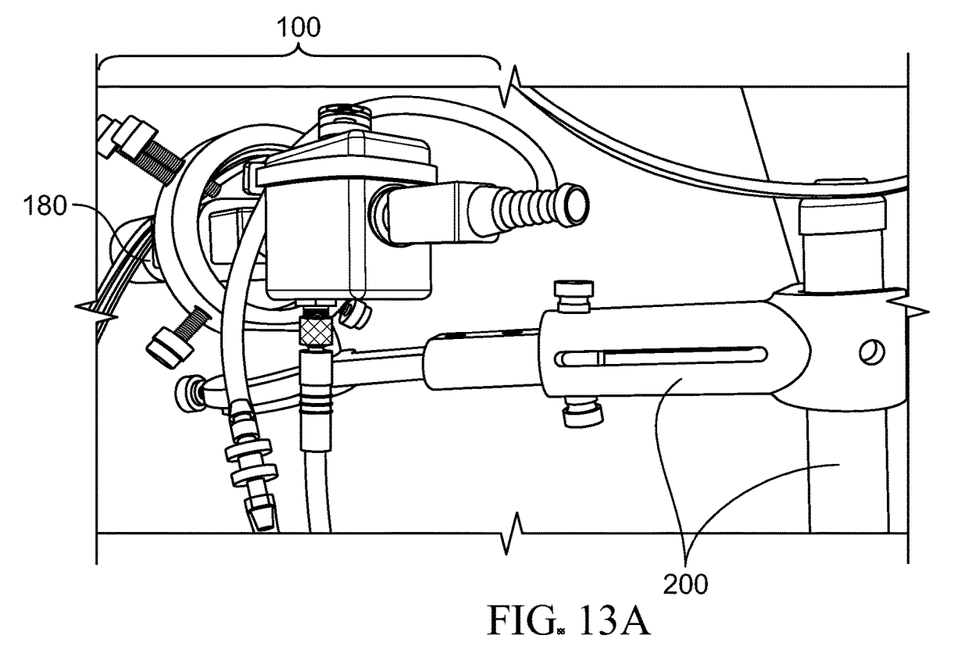
FIGS. 13A and 13B illustrate an embodiment of an OFMA connected to an alternative support that has a jointed arm for positioning the OFMA. The embodiment of the OFMA shown here includes an actuator mechanism. The jointed arm can be used to align the lens manipulator on the OFMA with an eye and the actuator mechanism can be used to advance or retract the lens manipulator.
Figure 13B:
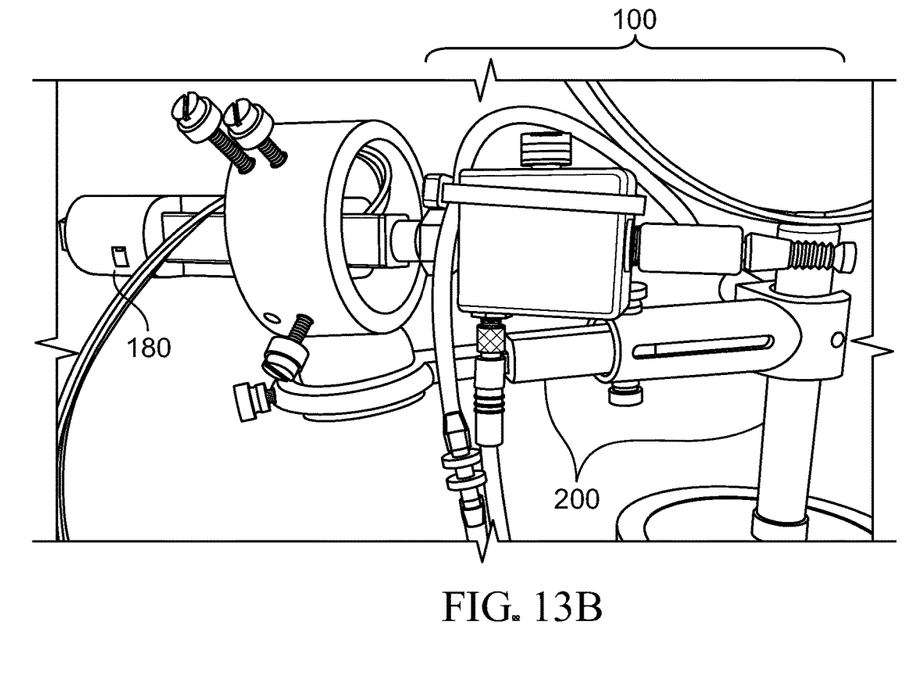

In another embodiment, the OFMA is operably attached to an actuator mechanism 180 that can be attached or mounted to an existing support 200. The actuator mechanism can be mounted on the support, with the OFMA thereon, in any direction or angle that facilitates removal or deposit of a contact lens on an eye. FIGS. 1, 3-7 illustrate an embodiment of an OFMA operably connected to a support, so that the lens manipulator moves in a substantially vertical direction. FIG. 12 shows one example of an OFMA 100 operably connected to an actuator mechanism 180 that can be attached to several types of supports. For example, slit lamps are a common apparatus in an ophthalmologist's office. They are typically mounted on a support that allows the slit lamp to be aligned with a patient's eye. An OFMA arranged on an actuator mechanism can be mounted on the same support used for a slit lamp. FIGS. 13A and 13B illustrate another non-limiting example of an OFMA with an actuator mechanism operably connected to a jointed arm extending from a head rest typically used in an ophthalmologist office. In this arrangement, the lens manipulator moves horizontally. Advantageously, embodiments of an OFMA of the subject invention can operate effectively either horizontally, vertically, or any angle or direction therebetween.

Figure 11A:
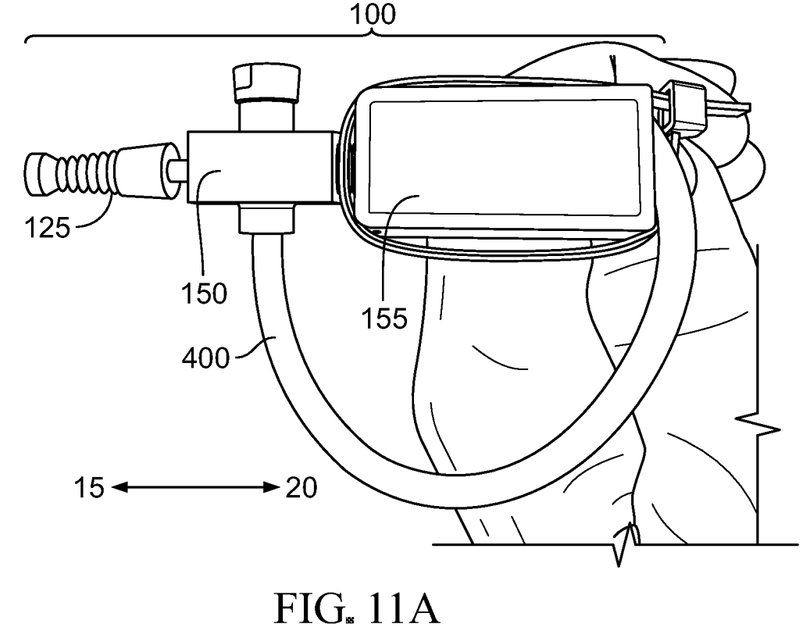
FIG. 11A is top plan view showing the attachment of a vacuum tube to the connector that creates a vacuum in the lens manipulator.
Figure 11B:
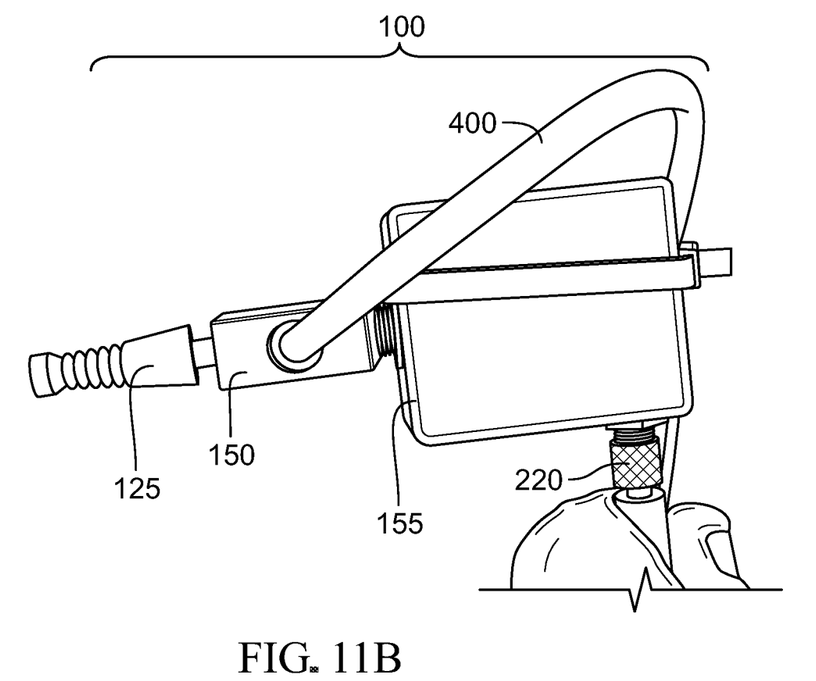
FIG. 11B is a side elevation view that shows the electrical attachment between the internal strain gauge load cell and the display.

In another embodiment, the OFMA is a hand-held device that includes the lens manipulator 125 arranged on the carrier 200 that is operably connected to the strain gauge load cell 155. With this embodiment, the OFMA is manipulated by hand to deposit or remove a contact lens from an eye and measures the forces. FIGS. 11A and 11B illustrate a non-limiting example of a hand-held or hand-manipulated OFMA.

With reference to FIG. 1, which illustrates one embodiment of an OFMA, it can be seen that a lens manipulator 125 is disposed on the proximal end 15 of a carrier 150. In one embodiment, the carrier comprises a rigid or semi-rigid material. By way of example, a carrier can be any of a variety of metals, plastics, nylon, glass, ceramics, combination thereof, or other suitable materials. In a one embodiment, the carrier has a substantially linear rod-shaped configuration, such as shown, for example, in FIGS. 1, 5, and 7. In alternative embodiments, a carrier has a non-linear or at least partially non-linear configuration. By way of example, all or some portion of the carrier can be curved or angled, which is not shown, but would be understood by a person skilled in the art.

In one specific embodiment, the carrier comprises a rigid transparent material or one capable of transmitting or conveying light along or through some portion of the carrier. This embodiment allows the proximal end of the carrier to be seen through the lens manipulator, so as to provide an additional guide to the user for positioning the eye above the lens manipulator. In one embodiment, the proximal end of the carrier is visible through the lens manipulator. Any of a variety of materials can be utilized for a carrier, through which light can pass, including, but not limited to, glass, acrylics, plastics, silicon, ceramics, and other materials or combinations thereof. Certain materials are specifically suited for light transmission, such as, but not limited to, polycarbonates and high-purity silica, and could also be utilized with embodiments of the subject invention. A carrier could also incorporate any of a variety of liquids, gels, gases, semi-solids, or other non-rigid materials, or combinations thereof. In one embodiment, the carrier is at least partially hollow, such that light is carried through the carrier. With this embodiment, it not required that the carrier comprise a light-transmitting material, as light can transmit through the hollow carrier. The use of materials and substances that are capable of transmitting or conveying light is a well-developed field. It is within the skill of a person trained in the art to determine which of one or more materials would be suitable for a carrier according to the subject invention. Such variations, which provide the same function in substantially the same way with substantially the same result, are within the scope of this invention.

At the proximal end of the carrier, there can be located a lens manipulator 125. FIGS. 2A, 2B, and 3-6 illustrate general embodiments of a lens manipulator. In one embodiment, a lens manipulator has an elongate form with a proximal end 15 portion in the shape of a concave suction cup 126 and a distal end 20 portion configured as a tube portion 127 in which the proximal end of the carrier is inserted. In another embodiment, the lens manipulator has a channel 128 therethrough that communicates the distal 20 and proximal ends 15 to provide a complete tubular form, such that the channel opens to form a pore 122 inside the suction cup portion, so as to communicate the distal end of the tube with the suction cup interior, an example of which is shown in FIGS. 1 and 2B. The channel can also facilitate visibility of the carrier through the lens manipulator, which can be advantageous when transmitting light, as mentioned above. In one embodiment, the tube portion 127 or the channel 128 of the lens manipulator 125 is fixedly attached to the proximal end of the carrier 150. In an alternative embodiment, the tube portion 127 or channel 128 of the lens manipulator 125 is removably attached to the proximal end of the carrier 150, such that different lens manipulators can be arranged on the carrier.

Figure 9:
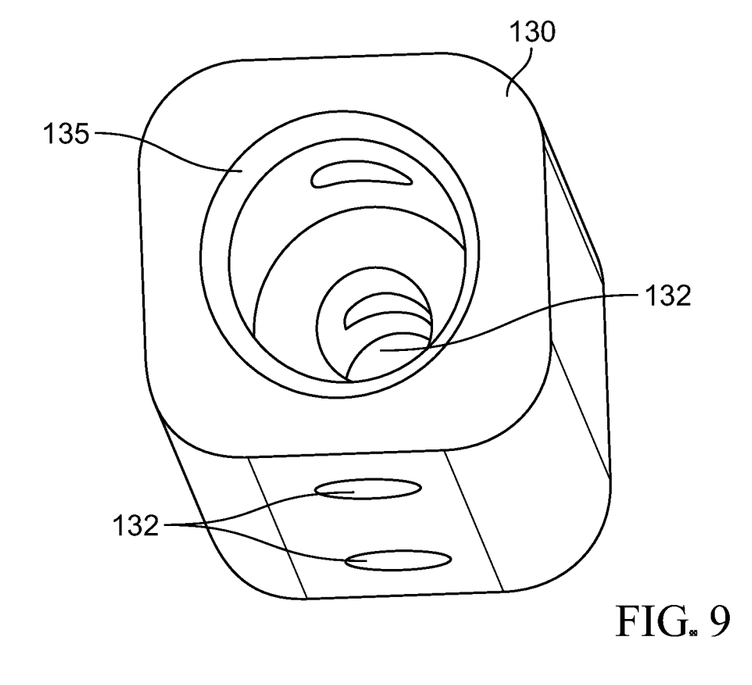
FIG. 9 shows one embodiment of an adaptor, according to the subject invention.

In an alternative embodiment, a lens manipulator has a closed distal end 20, such that it is not attached directly to the carrier 150. In one embodiment, an adaptor 130 is utilized to removably connect a lens manipulator 125 to a carrier 150. An adaptor can be configured to connect to one end of the carrier and to the distal end 20 of the lens manipulator at another end. In one embodiment, a distal end of the adaptor has one or more apertures 132 for removably receiving an end, such as the proximal end 15, of the carrier 150. In a further embodiment, the adaptor has one or more side bores 134 with locking screws that intersect with the aperture to apply force against the carrier in the aperture to inhibit movement of the carrier. In a further embodiment, the proximal end 15 of the adaptor has a port 135 for fittingly receiving an end of a lens manipulator. The port can secure the lens manipulator on the carrier sufficiently so as to inhibit removal from the carrier, when lens manipulator is used to remove a contact lens. FIG. 9 illustrates a non-limiting example of an adaptor, with an aperture, side bores, and a port. The locking screws are not shown, but would be understood by a person of skill in the art.

The suction cup can make contact with a contact lens for removing it from the surface or cornea of the eye. Alternatively, the suction cup can support a contact lens as it is inserted or deposited on the surface or cornea of the eye. The size of the suction cup 232 can vary, but ideally will have a linear diameter, i.e., the diameter across the proximal end of the cup, which is smaller than a contact lens thereon. In one embodiment, the linear diameter of a cup is between approximately 4 mm and approximately 8 mm. In a specific embodiment, the diameter of a cup is between approximately 5 mm and approximately 7 mm. In a more specific embodiment, the diameter of the cup is approximately 6 mm. Additionally, while the spherical diameter or radius of curvature of a cup can vary, it can, but is not required to, match that of a contact lens.

To facilitate attachment of the suction cup portion 126 of the lens manipulator 125 to a contact lens, a vacuum can be applied to the suction cup portion 126 of the lens manipulator. In one embodiment, at least a portion of the longitudinal length 25 of the carrier 150 has a hollow portion 152, such as shown, for example, in FIG. 5. In a further embodiment, the hollow portion in the carrier is in contact with or integral with the channel 128 of the lens manipulator. In a still further embodiment, a vacuum connector 400 is applied to the hollow portion of the carrier, such that a vacuum is exerted through the hollow portion of the carrier, through the channel in the lens manipulator and through the pore 122 in the suction cup portion. When applied to a contact lens, the vacuum can facilitate attachment or increase attachment of the suction cup portion to the contact lens. In a further embodiment, the vacuum is adjustable. The ability to apply a vacuum to the hollow portion of a carrier is within the ability of one of ordinary skill in the art and will not be described in detail here.

Figure 5:
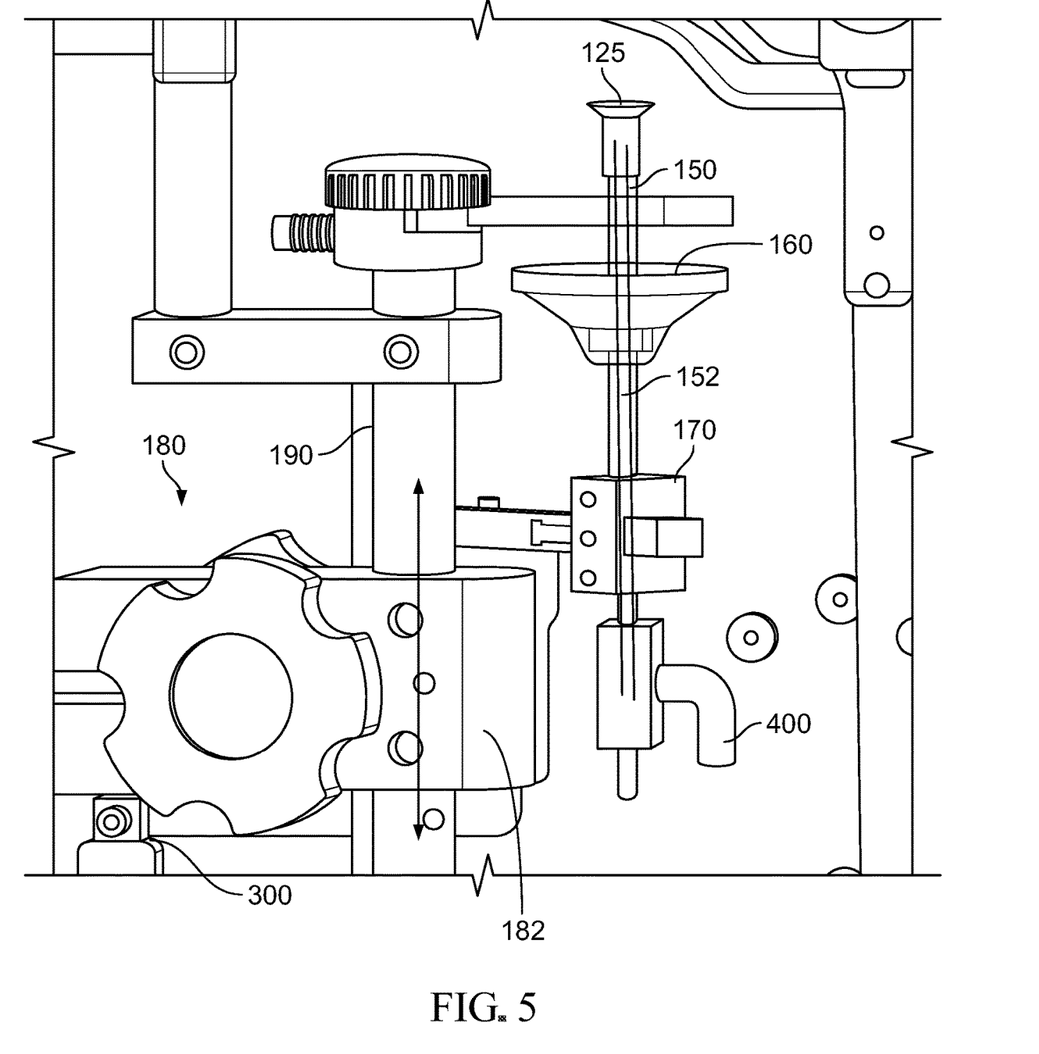
FIG. 5 shows an enlarged view of embodiments of an actuator mechanism, carrier, lens manipulator and bracket of an OFMA.
Figure 6:
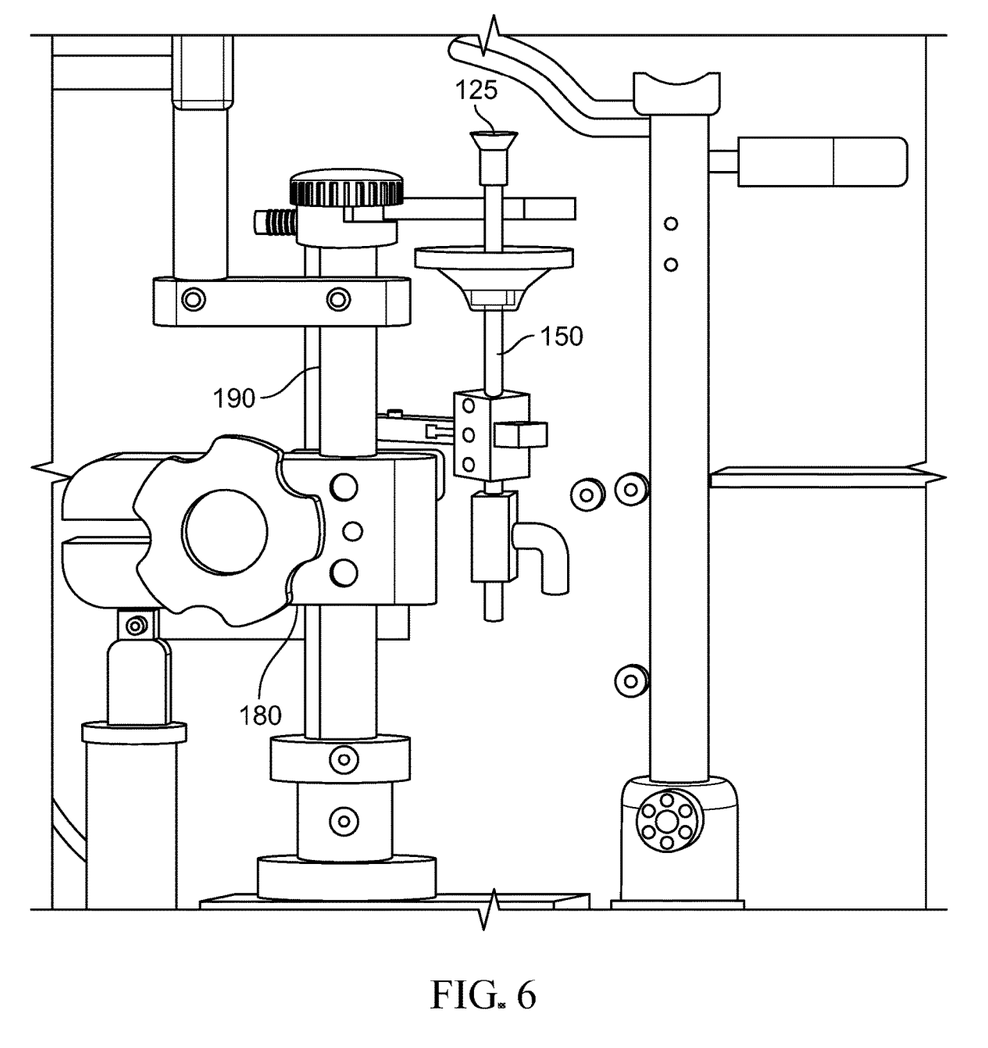
FIG. 6 shows another view of embodiments of an actuator mechanism, carrier, lens manipulator and bracket of an OFMA.
Figure 7:
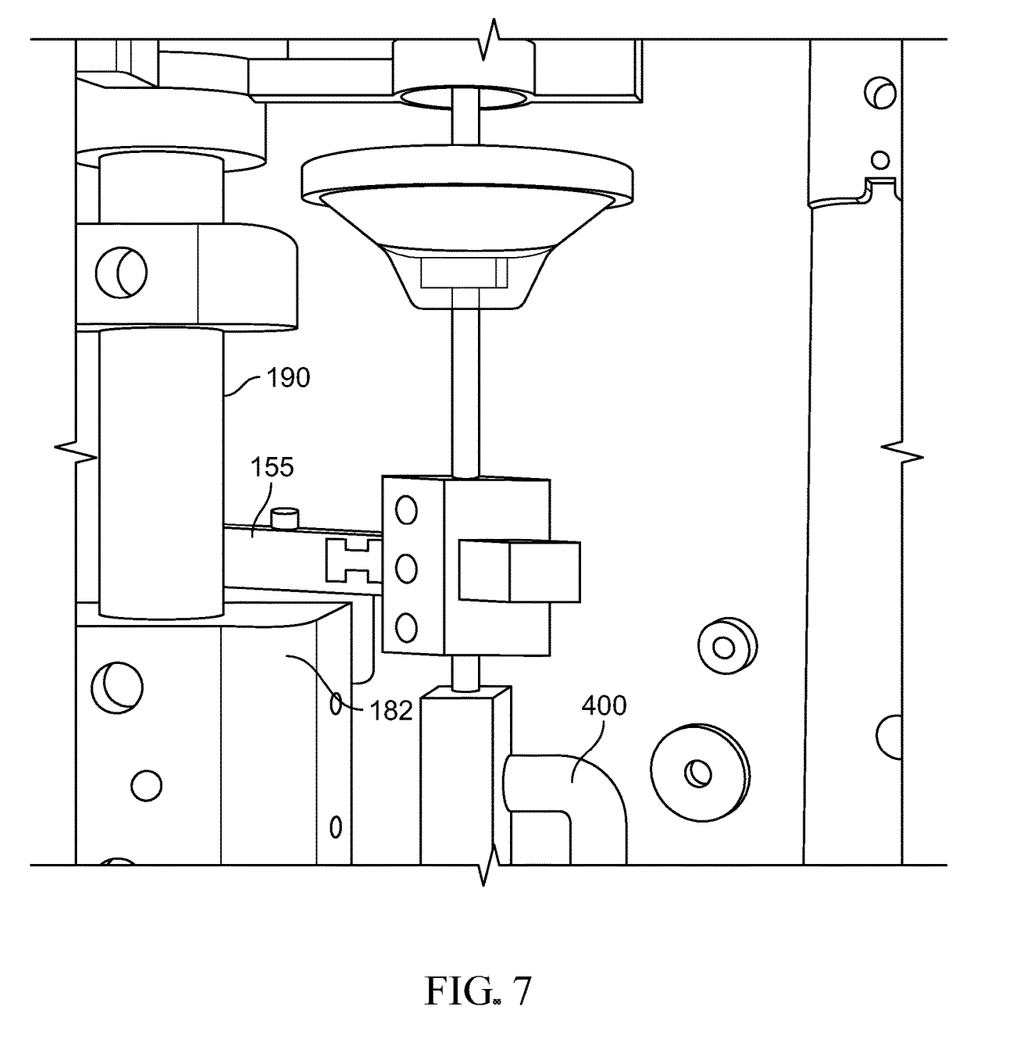
FIG. 7 shows an enlarged view of embodiments of a carrier and bracket and strain gauge load cell, according to embodiments of the subject invention.
Figure 8:
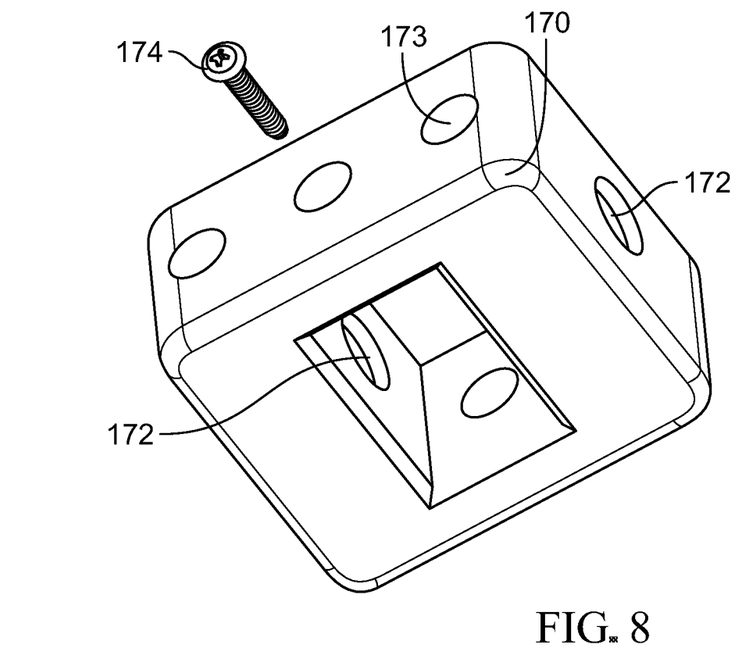
FIG. 8 shows a one embodiment of a bracket, according to the subject invention.

Inserting or removing a contact lens can be facilitated by the use of a fluid, such as a saline fluid, for lubrication. The fluid can be deposited on the eye before removing a contact lens or it can be used in the suction cup. In either instance, it is possible for the fluid to drip or flow down the lens manipulator and/or the carrier. In one specific embodiment, a lens sink 160 is arranged around the carrier 150 to contain any fluid that may drip of flow down the carrier. In one embodiment, a lens sink is attached to the carrier and moves when the carrier moves. FIGS. 1 and 5 illustrate embodiments of a lens sink.

Figure 4:
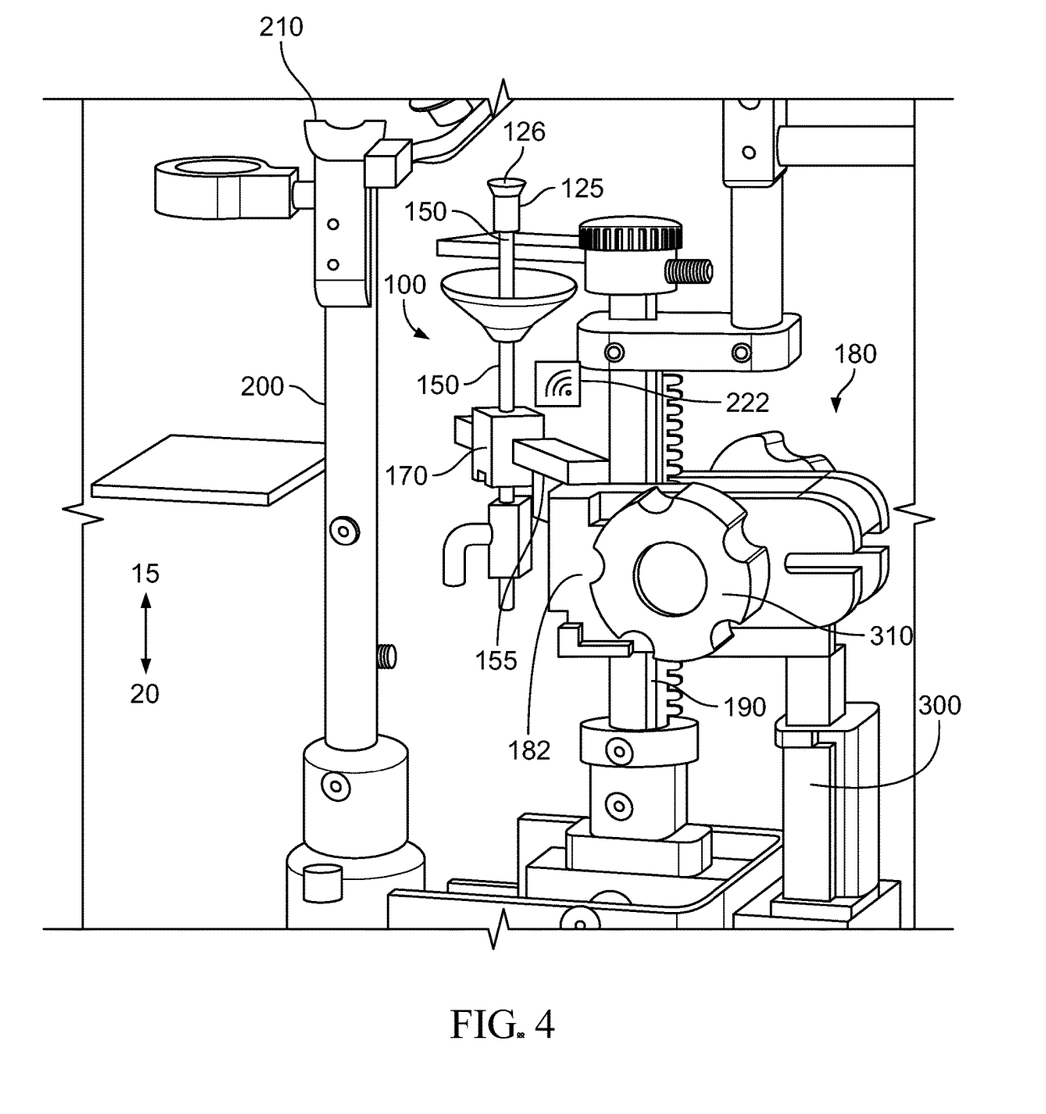
FIG. 4 shows an OFMA, according to one embodiment of the subject invention.
Figure 10:
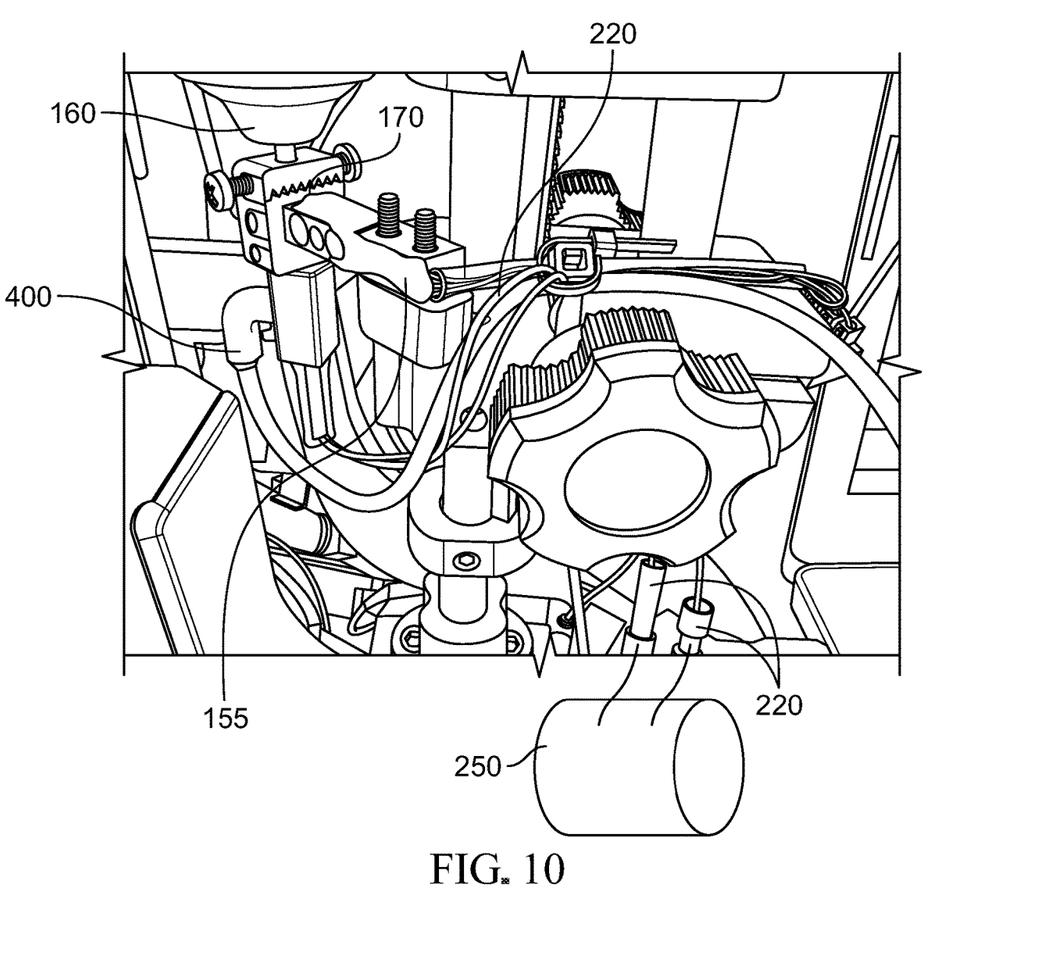
FIG. 10 shows an OFMA, according to embodiments of the subject invention, wherein the carrier is attached to a strain gauge load cell.

To determine the force required to remove a contact lens, the carrier can be operably connected to a device capable of detecting the force applied to the carrier 150. In one embodiment, the carrier is operably attached to a force detecting mechanism 154 that detects and measures force applied and/or deflection caused by the carrier. The carrier can be operably connected to the actuator mechanism 180. In one embodiment, the carrier is operably connected to the actuator mechanism through a strain gauge load cell 155 such as shown, for example in FIG. 1. In one embodiment, the carrier can operate as or be attached to a strain gauge load cell 155. The strain gauge load cell can be further operably connected to a display 159 that shows the force applied to the strain gauge load cell by the carrier. The strain gauge load cell can have mechanisms that facilitate direct or remote connection to the display. For example, the strain gauge load cell can have a cable 220 connection, such as shown in FIG. 10. Alternatively, the strain gauge can have a transmitter for wireless connection 222 to the display, such as shown in FIG. 4.

In one embodiment, shown for example, in FIGS. 11A and 11B, the OFMA is a portable or hand-held apparatus that includes a lens manipulator 125 arranged on a carrier 150 that is operably connected at or about the distal end 20 to a strain gauge load cell 155. The strain gauge load cell can detect forces applied in either direction along the longitudinal length of the carrier caused by the lens manipulator when depositing or removing a contact lens from an eye. A vacuum connector 400 can be connected to the lens manipulator 125 and/or the carrier 150, as described above. As shown in FIGS. 11A and 111B, this embodiment of an OFMA can be held and manipulated by hand. In another embodiment, the carrier 150, with the lens manipulator thereon, can be operably attached to a strain gauge load cell

Figure 2C:
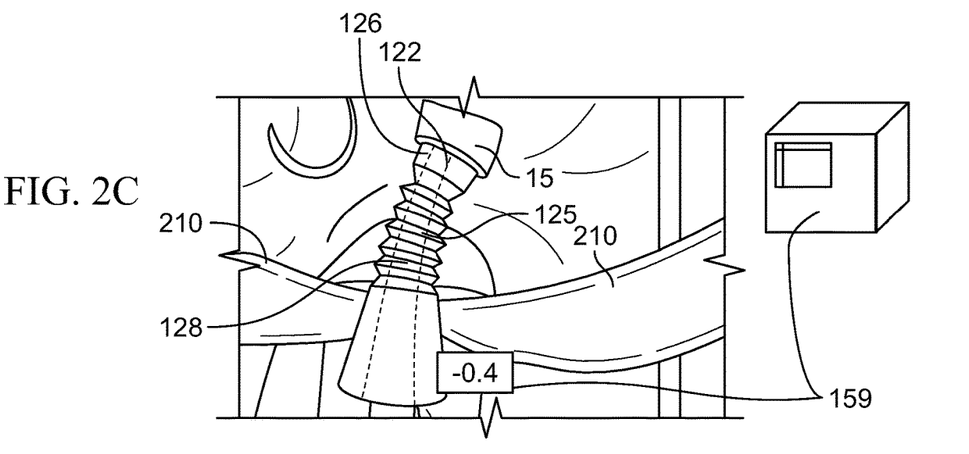

155. In a further embodiment, the carrier is operably connected at or about the proximal end 15 to a strain gauge load cell and the strain gauge load cell is operably attached to an actuator mechanism 180. Strain gauge load cells are well-known in the art and, as such, their operation will not be discussed in detail here. In one embodiment, a strain gauge load cell, as utilized with the subject invention, is configured to register and measure a downward or upward force applied to the strain gauge load cell. In a further embodiment, the upward or downward force on the strain gauge load cell is created by the force applied to the lens manipulator in removing or inserting a contact lens. The force is detectable by the strain gauge load cell through the carrier. In one embodiment, the actuator mechanism moves the carrier 150 and the lens manipulator 125 thereon toward the eye of a patient resting on or contacting the support 200. The lens manipulator can be advanced towards the eye until the suction cup portion engages with a contact lens on the eye. Once engaged, the actuator mechanism can be reversed so as to move the lens manipulator away from the eye. As the lens manipulator pulls the contact from the eye, force on the strain gauge load cell is measured. Alternatively, a contact lens can be placed on the suction cup portion of the and the lens manipulator advanced towards the eye until the suction cup is deposited on the eye. The force required to deposit the contact lens can be measured by the strain gauge load cell. FIG. 10 illustrates one embodiment of a strain gauge load cell configuration that can measure force applied to a carrier and the lens manipulator. FIGS. 2A, 2B, and 2C illustrate an example of a display 159 that shows the force applied to the strain gauge load cell during a process of removing a contact lens. FIG. 2A shows the lens manipulator attached to the contact lens. FIG. 2B shows the lens manipulator exerting force to remove the contact lens. FIG. 2C show the contact lens removed from the eye. Note the changes in force shown in the display. In a further embodiment, the strain gauge load cell is in operable connection with a recording device that records and/or saves the forces measured during a procedure. For example, the display can be operably connected to a computer readable memory 250 in which the forces measured are recorded and/or saved. The ability to record and save forces applied to a strain gauge load cell is known in the art.

The accuracy of measurements obtained by a force detecting mechanism 154, such as a strain gauge load cell 155, can depend at least upon the stability of the carrier 150. In one embodiment, the carrier is configured as a strain gauge load cell and is fixedly attached to the actuator mechanism by a cross-arm 153. In another embodiment, the carrier is fixedly attached to a strain gauge load cell, which is operably connected to the actuator mechanism. Force applied to the carrier is transmitted to the strain gauge load cell and measured, as described above. Motion of the actuator mechanism moving the carrier causes force to be applied to the carrier or the load cell by the lens manipulator when either removing or attaching a contact lens.

In some instances, it can be beneficial for the position of the carrier to be adjustable. For example, lens manipulators can vary in their dimensions, which can require the carrier to be adjustable. In one embodiment, the carrier is cooperatively engaged at or about the proximal end 15 of a cross-arm 153 or a strain gauge load cell 155 with a bracket 170. A bracket can have a orifice 172 through which some portion of the carrier can slide and one or more intersecting bore holes 173 in which locking screws 174 move to secure the position of the carrier in the orifice. FIG. 1 shows one example of a bracket that is cooperatively engaged by sliding over a cross-arm or strain gauge load cell. Alternative configurations that do not slide over the cross-arm or strain gauge load cell are also within the scope of the subject invention.

The carrier can be moved by an actuator mechanism 180. In one embodiment, a linear actuator mechanism is utilized to move the strain gauge load cell. In a further embodiment, the linear actuator is arranged, relative to the stabilizing arm to move the lens manipulator and the suction cup portion 125 substantially perpendicular to the surface or cornea of the eye. FIGS. 2A and 2B show close-up views of a lens manipulator in a substantially perpendicular direction relative to the eye as it removes a contact lens from the cornea. In one embodiment, an actuator mechanism is a rack and pinion system. In an alternative embodiment, the actuator mechanism is a pillow block bearing unit 182 arranged on a shaft 190, such as shown, for example, in FIGS. 3-7. Pillow block bearing units are known in the art. Such actuator mechanisms can provide smooth motion with minimal friction, which can be advantageous for obtaining small, precise measurements. In a further embodiment, the pillow block bearing unit is moved on the shaft by an electrical control mechanism 300, such as, for example, a piston. In an alternative embodiment, the pillow block bearing unit has a manual control 310. Any of a myriad of linear actuator mechanism 180 can be utilized with embodiments of the subject invention to facilitate movement of the stabilizer arm. It is also within the skill of a person trained in the art to determine alternative actuator mechanisms, devices, and methods by which the stabilizing arm can be actuated in a proximal 15/distal 20 direction. Thus, it should be understood that the mechanisms and methods by which the stabilizing arm are moved can vary. Such variations that provide the same function and substantially the same result are within the scope of this invention.

The force applied to the surface or cornea of an eye when removing a contact lens has been shown to have an effect on the eye. Understanding the forces applied to the eye by a contact lens can lead to better design and methods of using contact lenses, improve removal of specialty lenses, and assist handicapped individuals in using contact lenses. The ability to measure these forces heretofore has not been possible with current devices. The embodiments of the subject invention provide a device and methods by which these forces can now be measured, which can potentially lead to improvements in the manufacture, use, and safety of contact lenses.

The scope of the invention is not limited by the specific examples and suggested procedures and uses related herein since modifications can be made within such scope from the information provided by this specification to those skilled in the art.

All patents, patent applications, provisional applications, and other publications referred to or cited herein are incorporated by reference in their entirety, including all figures and tables, to the extent they are not inconsistent with the explicit teachings of this specification. Additionally, the entire contents of the references cited within the references cited herein are also entirely incorporated by reference.

What is claimed is:

1. An Ocular Force Measuring Apparatus, configured to be cooperatively engaged with a contact lens, comprising:
   a carrier having a proximal end and a distal end;
   a lens manipulator comprising a proximal end with a suction cup portion, adapted to cooperatively engage with the contact lens, and a distal end that operably connects to the proximal end of the carrier; and a strain gauge load cell, wherein the carrier is cooperatively connected to the strain gauge load cell;
wherein, when the suction cup portion is cooperatively engaged with the contact lens arranged on the surface of an eye, moving the carrier with the lens manipulator thereon away from the eye causes the lens manipulator to pull the contact lens thereby exerting a measureable force on the strain gauge load cell.

2. The Ocular Force Measuring Apparatus according to claim 1, further comprising:
 a channel in the lens manipulator that communicates the proximal end of the lens manipulator with the distal end, such that a pore is formed in the suction cup portion and the proximal end of the carrier is arranged within the distal end of the channel; and
 a hollow portion in at least a portion of the carrier, wherein the hollow portion communicates with the channel.

3. The Ocular Force Measuring Apparatus according to claim 2, further comprising a vacuum connector for operable attachment of a vacuum source to the hollow portion of the carrier, whereby a vacuum is exerted through the channel of the lens manipulator.

4. The Ocular Force Measuring Apparatus according to claim 1, further comprising a bracket that adjustably connects the carrier to the strain gauge load cell.

5. The Ocular Force Measuring Apparatus according to claim 1, further comprising an adaptor that operably connects the lens manipulator to the carrier, the adaptor comprising:
 an aperture for receiving the carrier; and
 a port in which the distal end of the lens manipulator is fittingly received.

6. The Ocular Force Measuring Apparatus according to claim 1, further comprising a display operably connected to the strain gauge load cell, such that the measureable force applied to the strain gauge load cell is visible on the display.

7. The Ocular Force Measuring Apparatus according to claim 1, further comprising:
 an actuator mechanism operably connected to the strain gauge load cell and utilized to the move the carrier.

8. The Ocular Force Measuring Apparatus according to claim 7, wherein the actuator is operably connectable to a support.

9. The Ocular Force Measuring Apparatus according to claim 8, wherein the support comprises at least one of slit lamp support and a jointed arm.

10. The Ocular Force Measuring Apparatus according to claim 8, wherein the actuator comprises a pillow block bearing unit.

11. A method for measuring the force utilized to remove a contact lens from an eye surface, the method comprising:
 obtaining an Ocular Force Measuring Apparatus according to claim 1,
  advancing the lens manipulator on the carrier towards the eye to cooperatively engage the suction cup portion with the contact lens thereon; and
  moving the carrier with the lens manipulator thereon away from the eye, so as to exert a measureable force on the strain gauge load cell equivalent to the force applied to the eye caused by pulling the contact lens from the surface thereof.

12. The method according to claim 11, wherein the Ocular Force Measuring Apparatus further comprises a display in operable connection with the strain gauge load cell and the method further comprises displaying the measureable force applied to the strain gauge load cell.

13. The method according to claim 11, wherein the Ocular Force Measuring Apparatus further comprises:
 a channel in the lens manipulator that communicates the proximal end of the lens manipulator with the distal end, such that a pore is formed in the suction cup portion and the proximal end of the carrier is arranged within the distal end of the channel; and
 a hollow portion in at least a portion of the carrier, wherein the hollow portion communicates with the channel,
 and the method further comprises exerting a vacuum through the hollow portion and the channel, such that when the suction cup portion engages with the contact lens, a vacuum is formed there between.

14. The method according to claim 13, wherein the Ocular Force Measuring Apparatus further comprises a vacuum connector and the method further comprises operably attaching the vacuum connector to the hollow portion and connecting a vacuum source to the vacuum connector so as to exert a vacuum through the hollow portion of the carrier and the channel of the lens manipulator.

15. The method according to claim 11, wherein the Ocular Force Measuring Apparatus further comprises an actuator mechanism to the move the carrier;
 wherein the method further comprises operatively attaching the actuator mechanism to a support.

16. The method according to claim 15, wherein the support comprises at least one of a slit lamp support and a jointed arm.

17. The method according to claim 15, wherein the actuator comprises a pillow block bearing unit.

18. The method according to claim 11, wherein the Ocular Force Measuring Apparatus further comprises a bracket comprising at least one orifice for receiving the carrier and the method further comprises cooperatively attaching the carrier to the strain gauge load cell with the bracket.

19. The method according to claim 11, wherein the Ocular Force Measuring Apparatus further comprises an adaptor comprising:
 an aperture for receiving the carrier;
 a port in which the distal end of the lens manipulator is fittingly received,
 and the method further comprises arranging the carrier within the aperture and arranging the distal end of the lens manipulator within the port.

* * * * *